US012609191B2

(12) United States Patent
Li et al.

(10) Patent No.: US 12,609,191 B2
(45) Date of Patent: Apr. 21, 2026

(54) DATA PROCESSING METHOD AND DEVICE

(71) Applicants:Beijing Zitiao Network Technology Co., Ltd., Beijing (CN); LEMON INC., Grand Cayman (KY)

(72) Inventors: Li Li, Beijing (CN); Matthew Boring, Los Angeles, CA (US); Dongpo Li, Beijing (CN); Yun Liao, Beijing (CN); Runchen Zhao, Los Angeles, CA (US); Tianjia Sun, Los Angeles, CA (US); Guanqun Zhang, Beijing (CN); Can Jin, Los Angeles, CA (US)

(73) Assignees: Beijing Zitiao Network Technology Co., Ltd., Beijing (CN); LEMON INC., Grand Cayman (KY)

( * ) Notice: Subject to any disclaimer, the term of this patent is extended or adjusted under 35 U.S.C. 154(b) by 1 day.

(21) Appl. No.: 18/605,328

(22) Filed: Mar. 14, 2024

(65) Prior Publication Data

US 2024/0312596 A1 Sep. 19, 2024

(51) Int. Cl.
G16H 20/30 (2018.01)
G06N 3/126 (2023.01)
G16H 40/67 (2018.01)

(52) U.S. Cl.
CPC ............. G16H 20/30 (2018.01); G06N 3/126 (2013.01); G16H 40/67 (2018.01)

(58) Field of Classification Search
CPC ........ G16H 20/30; G16H 40/67; G06N 3/126; A61B 5/1118; A61B 5/1121; A61B 5/6803; A61B 5/6825; A61B 5/6828; A61B 5/72; A61B 5/742
USPC ........................................................ 705/2–3
See application file for complete search history.

(56) References Cited

U.S. PATENT DOCUMENTS

2016/0346614 A1* 12/2016 Kirby ..................... G06Q 10/10
2018/0373926 A1* 12/2018 Mizuochi ................. A61B 5/11
2023/0138673 A1* 5/2023 Crawford .............. G16H 20/10
600/365

FOREIGN PATENT DOCUMENTS

CN         115560750 A      1/2023
WO      WO-2016038585 A1 * 3/2016    ........... A61B 5/7275

OTHER PUBLICATIONS

Leone et al., Ambient and Wearable Sensor Technologies for Energy Expenditure Quantification of Ageing Adults. Sensors (Basel). Jun. 29, 2022; 22(13):4893. doi: 10.3390/s22134893. PMID: 35808387; PMCID: PMC9269397 (Year: 2022).*
Álvarez-García et al., 2020, A Survey on Energy Expenditure Estimation Using Wearable Devices, ACM Comput. Surv. 53, 5, Article 91 (Sep. 2021), 35 pages. https://doi.org/10.1145/3404482 (Year: 2020).*
"There are not many excuses left for not exercising! VR exercise is the new fitness trend", Firewood Chopping, vol. 15, No. 51, Oct. 10, 2022, pp. 1-14.

* cited by examiner

*Primary Examiner* — Joy Chng

(57) ABSTRACT

The present disclosure provides a data processing method and device, the method includes: acquiring exercise data of a user in a preset time period and a physical parameter preset by the user, wherein the exercise data comprises exercise data of a head, a hand and a leg of the user; and inputting the exercise data and the physical parameter into a pre-trained energy determination model for processing to obtain energy consumed by the user in the preset time period.

17 Claims, 3 Drawing Sheets

| |
|---|
| Acquiring the exercise data of a user in a preset time period and the physical parameter preset by the user |

S201

| |
|---|
| Inputting the exercise data and the physical parameter into a pre-trained energy determination model for processing to obtain the energy consumed by the user in a preset time period |

S202

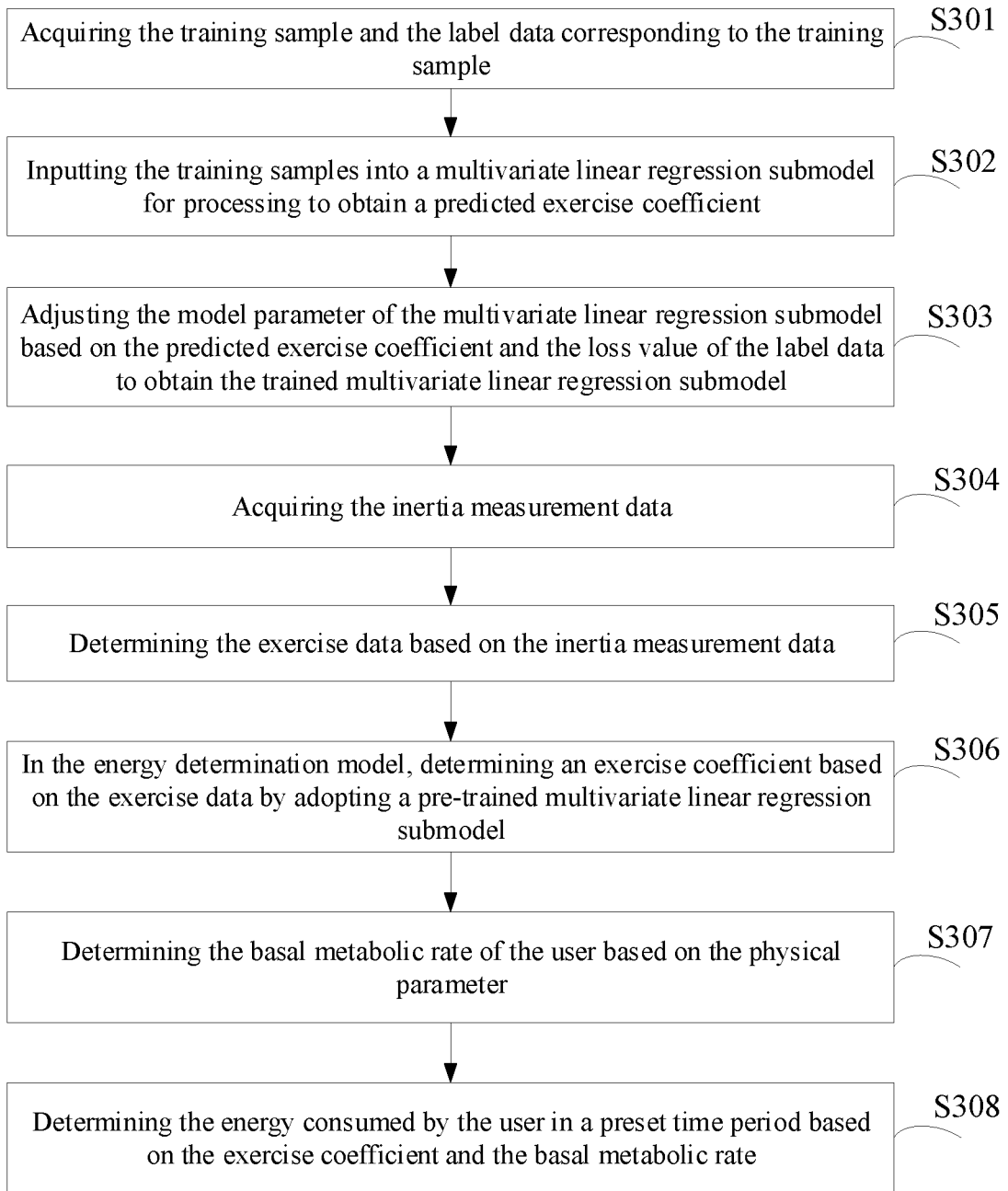

Acquiring the training sample and the label data corresponding to the training sample ⟋S301

Inputting the training samples into a multivariate linear regression submodel for processing to obtain a predicted exercise coefficient ⟋S302

Adjusting the model parameter of the multivariate linear regression submodel based on the predicted exercise coefficient and the loss value of the label data to obtain the trained multivariate linear regression submodel ⟋S303

Acquiring the inertia measurement data ⟋S304

Determining the exercise data based on the inertia measurement data ⟋S305

In the energy determination model, determining an exercise coefficient based on the exercise data by adopting a pre-trained multivariate linear regression submodel ⟋S306

Determining the basal metabolic rate of the user based on the physical parameter ⟋S307

Determining the energy consumed by the user in a preset time period based on the exercise coefficient and the basal metabolic rate ⟋S308

Fig. 3

DATA PROCESSING METHOD AND DEVICE

CROSS REFERENCE TO RELATED APPLICATION

This application claims priority from Chinese Patent Application No. 202310244753.6, filed on Mar. 14, 2023, the contents of which are hereby incorporated by reference in their entirety for all purposes.

TECHNICAL FIELD

The present disclosure relates to the field of data processing, and in particular, to a data processing method and device.

BACKGROUND

During exercise of the user, the energy consumption data is the basic index of the exercise effect, the expression of the core data of the exercise effect of the user, and the exercise index that users are most concerned about. Among them, the wearable devices can be used in the exercise scenario of the user. If the energy consumed by users during exercise when using the wearable devices can be provided to the user in real time and accurately, the experience of the user will be greatly improved.

SUMMARY

The embodiment of the disclosure provides a data processing method and device.

The embodiment of the present disclosure provides a data processing method applied to a wearable device, wherein the data processing method comprises: acquiring exercise data of a user in a preset time period and a physical parameter preset by the user, wherein the exercise data comprises exercise data of a head, a hand and a leg of the user; and inputting the exercise data and the physical parameter into a pre-trained energy determination model for processing to obtain energy consumed by the user in the preset time period.

The embodiment of the present disclosure provides a data processing device applied to a wearable device, wherein the data processing device comprises:

an acquisition unit configured to acquire exercise data of a user in a preset time period and a physical parameter preset by the user, wherein the exercise data comprises exercise data of a head, a hand and a leg of the user; and a processing unit configured to input the exercise data and the physical parameter into a pre-trained energy determination model for processing to obtain energy consumed by the user in the preset time period.

The embodiment of the present disclosure provides an electronic device, comprising at least one processor and a memory;

the memory stores computer-executable instructions;

the at least one processor execute the computer-executable instructions stored by the memory to cause the at least one processor to perform the data processing method provided by the above first aspect.

The embodiment of the present disclosure provides a non-transitory computer readable storage medium having stored thereon computer executable instructions which, when executed by a processor, implement the data processing method provided by the above first aspect.

The embodiment of the present disclosure provides a computer program product including computer executable instructions which, when executed by a processor, implement the data processing method provided by the above first aspect.

BRIEF DESCRIPTION OF THE DRAWINGS

In order to more clearly illustrate the embodiments of the present disclosure or the technical solutions in the related art, the drawings used in the embodiments or the description of the related art will be briefly described below, and it is obvious that the drawings in the following description are some embodiments of the present disclosure, and those skilled in the art can obtain other drawings without paying creative effort.

FIG. 3 is a flow chart illustrating steps of another data processing method provided by an embodiment of the present disclosure;

DETAILED DESCRIPTION

To make the objects, technical solutions and advantages of the embodiments of the present disclosure more apparent, the technical solutions in the embodiments of the present disclosure will be described clearly and completely with reference to the drawings in the embodiments of the present disclosure, and it is obvious that the described embodiments are some, but not all embodiments of the present disclosure. All other embodiments, which can be derived by a person skilled in the art from the embodiments disclosed herein without paying any creative effort, shall fall within the protection scope of the present disclosure.

The wearable device includes: Virtual (VR) devices. The wearable device can be applied to the exercise scenario. On one hand, the wearable devices aiming at exercise, health and health tracking have great development potential, and on the other hand, the characteristics of the VR devices, such as scenarization, enjoyment, data tracking specialty and convenience, can attract users with exercise needs. During exercise of the user, the energy consumption data is the basic index of the exercise effect, the expression of the core data of the exercise effect of the user, and the exercise index that users are most concerned about. At present, the energy consumption of exercise is estimated by using related data on the head-mounted display and the handle. This algorithm does not consider the consumption of the exercise energy of the lower limbs, and a feasible algorithm is not provided for determining the energy consumed by the exercise of the user, so that it cannot provide the user with the real-time and accurate energy consumption data.

Based on the above problem, the data processing method and device provided by the present disclosure acquire exercise data of a user in a preset time period and a physical parameter preset by the user, wherein the exercise data includes exercise data of a head, a hand and a leg of the user; and input the exercise data and the physical parameter into a pre-trained energy determination model for processing to obtain energy consumed by the user in the preset time period. The present disclosure, based on the exercise data acquired from the head, the hand and the leg of the user, realizes the comprehensive collection of the exercise data, and the energy consumed by the user in the exercise process can be determined accurately in real time by determining the energy consumption through the pre-trained energy determination model.

Figures 1, 2:
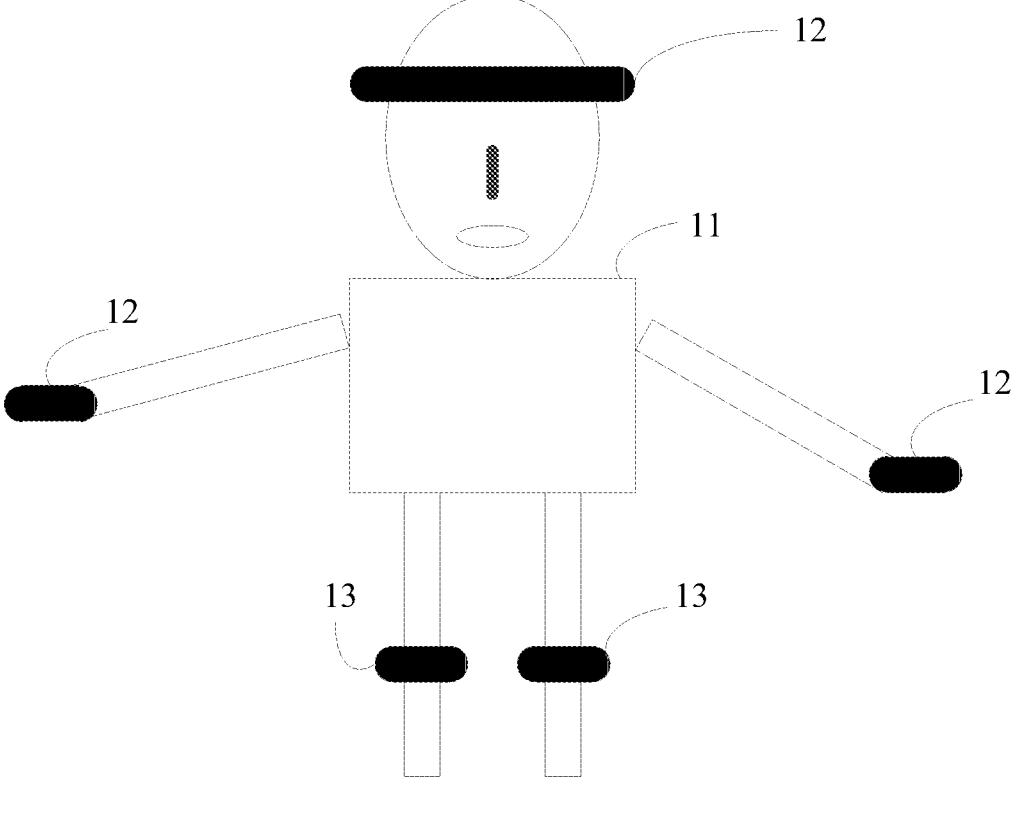
FIG. 1 is an exemplary diagram of an application scenario provided by an embodiment of the present disclosure.
FIG. 2 is a flowchart illustrating steps of a data processing method provided by an embodiment of the present disclosure.

Referring to FIG. 1, FIG. 1 is an exemplary diagram of an application scenario provided by an embodiment of the present disclosure. As shown in FIG. 1, it includes: a user 11 and a wearable device, wherein the wearable device includes: a head-mounted display 12, a handle 13 and a leg tracking device 14. The wearable device is provided with an Inertial Measurement Unit (IMU), and the IMU can measure inertial measurement data of a corresponding part.

The above application scenario is only one of the scenario examples, and the embodiments of the present disclosure may be applied to any wearable device applied to an exercise scenario.

Referring to FIG. 2, a schematic flow chart of a data processing method provided by an embodiment of the disclosure is shown. As shown in FIG. 2, when applied to a wearable device, the data processing method specifically includes the following step:

S201, acquiring the exercise data of a user in a preset time period and the physical parameter preset by the user.

The exercise data includes exercise data of a head, hands and legs of the user.

In the present disclosure, by collecting exercise data of the head, the hands, and the legs, the collected exercise data of the user can be made more complete, and based thereon, the determination of the energy consumed by the user is made more accurate.

Further, the physical parameter preset by the user include: height, weight and so on. For different users, when the height and the weight are different, the energy consumed even though performing the same exercise is different, so when the energy consumed by the user is determined, the accuracy of determining the consumed energy can be improved by considering the physical parameter preset by the user.

In the present disclosure, the physical parameter of the user is acquired and utilized at the user's consent.

S202, inputting the exercise data and the physical parameter into a pre-trained energy determination model for processing to obtain the energy consumed by the user in a preset time period.

The energy determination model is a pre-trained mathematical model, can calculate the exercise data and the physical parameter input into the energy determination model, and can quickly and accurately obtain the energy consumed by the user in a preset time period.

In summary, the data processing method and device provided by the embodiment are applied to a wearable devices and include the following steps: acquiring exercise data of a user in a preset time period and a physical parameter preset by the user, wherein the exercise data includes exercise data of a head, a hand and a leg of the user; and inputting the exercise data and the physical parameter into a pre-trained energy determination model for processing to obtain energy consumed by the user in the preset time period. The present disclosure, based on the exercise data acquired from the head, the hand and the leg of the user, realizes the comprehensive collection of the exercise data, and the energy consumed by the user in the exercise process can be determined accurately in real time by determining the energy consumption through the pre-trained energy determination model.

Referring to FIG. 3, a schematic flowchart of another data processing method provided by an embodiment of the disclosure is shown. As shown in FIG. 3, when applied to a wearable device, the data processing method specifically includes the following steps:

S301, acquiring the training sample and the label data corresponding to the training sample.

The training samples are exercise data serving as samples, and the label data are exercise coefficients corresponding to the training samples.

In the present disclosure, a plurality of training samples are included, each training sample including a set of exercise data, for example: the moving distance $x_1$ of the head-mounted display, the square $x_2$ of the average linear velocity, the square $x_3$ of the average angular velocity, the total moving distance $x_4$ of the handle, the average linear velocity $x_5$, the average angular velocity $x_6$, the square $x_7$ of the average angular velocity and the square $x_8$ of the average acceleration of the leg tracking device, and the tag data y are the numerical values greater than 1.

S302, inputting the training samples into a multivariate linear regression submodel for processing to obtain a predicted exercise coefficient.

The mathematical expression of the multivariate linear regression submodel is $N=W^T X$, wherein W is a model parameter of the multivariate linear regression submodel, $W=\{\alpha_1, \alpha_2, \alpha_3, \alpha_4, \ldots, \alpha_n\}$, $X=\{x_1, x_2, x_3, x_4, \ldots, x_n\}$, wherein n is a positive integer greater than 1 and is specifically the number of exercise data in a set of exercise data, and as shown above, includes eight exercise data.

Specifically, W is set as an initial default value, a set of exercise data is applied to the formula $N=W^T X$ to obtain a predicted exercise coefficient $N_1$.

S303, adjusting the model parameter of the multivariate linear regression submodel based on the predicted exercise coefficient and the loss value of the label data to obtain the trained multivariate linear regression submodel.

The calculation formula of the loss value is as follows:

$$S = \left\| y - W^T X \right\|_2^2 + \lambda \| W \|_2^2.$$

$\lambda$ is the coefficient for preventing over-fitting.

In addition, if the loss value S is larger than the threshold value for the loss value, the loss value is adopted to adjust the model parameter W, then the set of exercise data is continuously adopted to train the multiple linear regression submodel until S is smaller than the threshold value of the loss value, then the next set of exercise data is continuously adopted to carry out the training, and the model parameter with the smallest $\Sigma S$ is selected as the model parameter of the trained multiple linear regression submodel.

Further, the model parameter of the multiple linear regression submodel is greater than 0, specifically, the constraint $\alpha_i$ is greater than 0, wherein i is 1 to n.

In addition, during the training process, the optimal model parameter can be selected by adopting a cross validation method. Specifically, a plurality of data samples are included, and the plurality of data samples are divided into m parts. Then m−1 parts (there are m ways to choose) of the data samples are selected as the training samples to carry out the training, m model parameters are correspondingly obtained, then the rest data sample are used as verification samples to determine the optimal model parameters of the m model parameters, and the optimal model parameters are used as the final model parameters of the multiple linear regression submodel for online use.

Illustratively, 60 training samples are included and divided into 3 parts, namely a first set of data sample (20 training samples), a second set of data sample (20 training samples) and a third set of data sample (20 training samples). Firstly, a multivariate linear regression submodel is trained by adopting a first set of data sample and a second set of data sample to obtain a model parameter A, and then the model parameter A is verified by adopting a third data sample to obtain a verification result a. Then, the multivariate linear regression submodel is trained by adopting the first set of data sample and the third set of data sample to obtain a model parameter B, and then the model parameter B is verified by adopting the second set of data sample to obtain a verification result b. Then, the multivariate linear regression submodel is trained by adopting the second set of data sample and the third set of data sample to obtain a model parameter C, and then the model parameter C is verified by adopting the second set of data sample to obtain a verification result c. If the best verification result among the verification results a, b, and C is the verification result c, the model parameter C can be determined as the final model parameter of the multivariate linear regression submodel.

In the present disclosure, the verification result can employ a formula $$R_{adj}^2 = 1 - \frac{(1 - R^2)(N - 1)}{N - K - 1}.$$

$$R_{adj}^2$$

represents the verification result, namely the determination coefficient for correction, and is used for representing the fitting degree of the multivariate linear regression submodel. The larger the fitting degree of the multivariate linear regression submodel is, the higher the fitting degree of the multivariate linear regression submodel is. N represents the number of verification samples, for example, 20 as described above, and K represents the number of variables in the exercise data, for example, 8 variables as described above. R is a determination coefficient, and is also used to indicate the fitting degree of the model, and the specific determination method is not limited herein.

In the disclosure, the multivariate linear regression submodel with good quality can be trained through the method.

S304, acquiring the inertia measurement data.

In the present disclosure, the inertial measurement data is acquired by a wearable device of a user. The inertial measurement data includes: linear acceleration and angular acceleration.

The wearable device includes: a head-mounted display, a handle and a leg tracking device attached to the leg of the user. The handle and the leg tracking device are in communication connection with the head-mounted display. The head-mounted display, the handle and the leg tracking device respectively include an inertial measurement sensor. It is understood that the inertial measurement data of the present disclosure includes at least one of the inertial measurement data of the head-mounted display, the inertial measurement data of the handle, and the inertial measurement data of the leg tracking device.

In particular, referring to FIG. 1, the head-mounted display 12 may be a head-mounted display device that is worn on the head of the user, through which the user can see some data, such as the calories consumed. Further, the head-mounted display 12 may monitor the inertial measurement data of the user's head. The handle may be a device held in the hand of the user and the handle may monitor the inertial measurements of the hand of the user. The leg tracking device may be strapped to the thigh and/or calf of the user for tracking the inertial measurement data of the user's leg.

S305, determining the exercise data based on the inertia measurement data.

Determining exercise data based on the inertial measurement data includes at least one of:

1) determining the moving distance, the square of the average linear velocity and the square of the average angular velocity of the head-mounted display in the preset time period based on the inertia measurement data of the head-mounted display;

2) determining the total moving distance, the average linear speed and the average angular speed of the handle based on the inertia measurement data of the handle; and 3) determining the square of the average angular velocity and the square of the average acceleration of the leg tracking device based on the inertial measurement data of the leg tracking device.

In the present disclosure, the preset time may be set as needed, for example, to 3000 ms, that is, the moving distance of the head-mounted display, the square of the average linear velocity of the head-mounted display, and the square of the average angular velocity of the head-mounted display within every 3000 ms are calculated.

Furthermore, how to determine the exercise data based on the inertial measurement data of the head-mounted display is not limited by the present disclosure.

Further, the exercise data that may be determined by the present disclosure may include one or more of: a moving distance of the head-mounted display, a square of the average linear velocity and a square of the average angular velocity, a total moving distance, the average linear velocity and the average angular velocity of the handle, a square of the average angular velocity and a square of the average acceleration of the leg tracking device.

For example, in the process of user's exercise, the legs and the head of the user are not fixed, and only the hands move, the user can only carry the handle, and then only the movement data corresponding to the handle can be acquired.

In the present disclosure, it is also necessary to unify the units of the exercise data. For example, if the moving distance of the head-mounted display in a preset time (3000 ms) is L1 (cm), the moving distance may be unified as how many centimeters are moved per minute, and the moving distance is (L1/3000)×1000×60. Other exercise data may also be unified into data in units of minutes for time and centimeters for distance.

S306, in the energy determination model, determining an exercise coefficient based on the exercise data by adopting a pre-trained multivariate linear regression submodel.

The mathematical expression of the multivariate linear regression submodel is as follows:

$$N = \alpha_1 P_1 + \alpha_2 P_2 + \dots + \alpha_m P_m$$

In the above equation, m represents the number of exercise data, i.e., the above 8 exercise data, and α represents the parameter obtained by the above training. For example, $P_1$ represents a moving distance of the head-mounted display, $P_2$ represents a square of an average linear velocity of the head-mounted display, $P_3$ represents a square of an average angular velocity of the head-mounted display, $P_4$ represents a total moving distance of the (two) handles, $P_5$ represents an average linear velocity of the (two) handles, $P_6$ represents an average angular velocity of the leg tracking device, $P_7$ represents a square of an average angular velocity of the leg tracking device, $P_8$ represents a square of an average acceleration of the leg tracking device.

S307, determining the basal metabolic rate of the user based on the physical parameter.

In the present disclosure, the physical parameter includes: age, gender, height and weight. The basal metabolic rate can be expressed by Harris-Benedict equation. The equation is as follows:

$$\text{Male: } C = 66.47 + 13.75 \times \text{weight(kg)} + 5.0033 \times \text{height(cm)} - 6.775 \times \text{age}$$

$$\text{Female: } C = 65.51 + 9.563 \times \text{weight(kg)} + 1.850 \times \text{height(cm)} - 4.676 \times \text{age}$$

From the above, the basal metabolic rate for one day can be obtained, and further, the basal metabolic rate per minute can be calculated as $D=C/1440$.

S308, determining the energy consumed by the user in a preset time period based on the exercise coefficient and the basal metabolic rate.

The energy consumed by the user per minute can be obtained by the product of the exercise coefficient and the basal metabolic rate. In the present disclosure, it is necessary to determine the consumed energy J of the user within a preset time T. $J=N \times D \times T/60$. N represents the exercise coefficient per minute. D represents the basal metabolic rate per minute. T represents a preset time in seconds.

In the present disclosure, the exercise data of a leg may be tracked using a leg tracking device attached to the leg, and the energy consumed by a user within a preset time may be accurately and efficiently determined using a pre-trained energy determination model in combination with the exercise data of the head and the hand.

Figure 4:
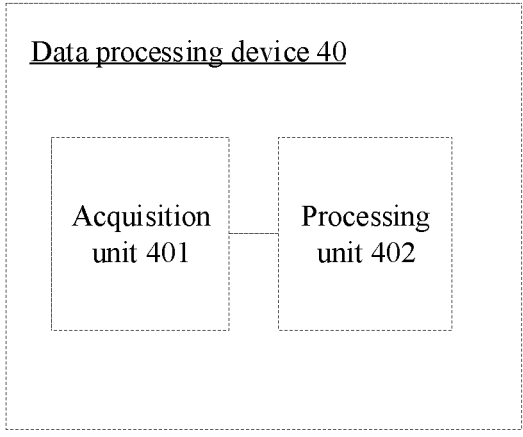
FIG. 4 is a block diagram of a data processing device provided by an embodiment of the present disclosure.

Corresponding to the data processing method of the above embodiments, FIG. 4 is a block diagram of a data processing device 40 provided by an embodiment of the present disclosure. For ease of illustration, only the parts relevant to embodiments of the present disclosure are shown. As shown in FIG. 4, the data processing device 40 specifically includes: an acquisition unit 401 and a processing unit 402, wherein:

the acquisition unit 401 is configured to acquire exercise data of a user in a preset time period and a physical parameter preset by the user, wherein the exercise data includes exercise data of a head, a hand and a leg of the user;

the processing unit 402 is configured to input the exercise data and the physical parameter into a pre-trained energy determination model for processing to obtain energy consumed by the user in the preset time period.

In some embodiments, the processing unit 402 is specifically configured to in the energy determination model, adopt a pre-trained multivariate linear regression submodel to determine an exercise coefficient based on the exercise data; determine a basal metabolic rate of the user based on the physical parameter; and determine the energy consumed by the user in the preset time period based on the exercise coefficient and the basal metabolic rate.

In some embodiments, a training unit (not shown) is also included, and the training unit is specifically configured to: acquire a training sample and label data corresponding to the training sample, wherein the training sample is used as the exercise data of a sample, and the label data is the exercise coefficient corresponding to the training sample; input the training sample into a multiple linear regression submodel for processing to obtain a predicted exercise coefficient; and adjust a model parameter of the multivariate linear regression submodel based on the predicted exercise coefficient and a loss value of the label data to obtain a trained multivariate linear regression submodel.

In some embodiments, the model parameter of the multivariate linear regression submodel is greater than 0.

In some embodiments, the obtaining unit 401 is specifically configured to acquire inertial measurement data, the inertial measurement data being acquired by the wearable device of the user; and determine the exercise data based on the inertia measurement data.

In some embodiments, the wearable device includes: a head-mounted display, a handle and a leg tracking device, wherein the leg tracking device is attached to the leg of the user, the handle and the leg tracking device are in communication connection with the head-mounted display, and the head-mounted display, the handle, and the leg tracking device include an inertial measurement sensor, respectively.

In some embodiments, the acquisition unit is configured to determine the exercise data based on the inertial measurement data for at least one of:

determining a moving distance, a square of an average linear velocity and a square of an average angular velocity of the head-mounted display in the preset time period based on the inertial measurement data of the head-mounted display;

determining a total moving distance, an average linear speed and an average angular speed of the handle based on the inertia measurement data of the handle; and determining a square of an average angular velocity and a square of an average acceleration of the leg tracking device from the inertial measurement data of the leg tracking device.

The data processing device provided in this embodiment may be used to implement the technical solution of the embodiment of the data processing method, and the implementation principle and the technical effect are similar, which are not described herein again.

Figure 5:
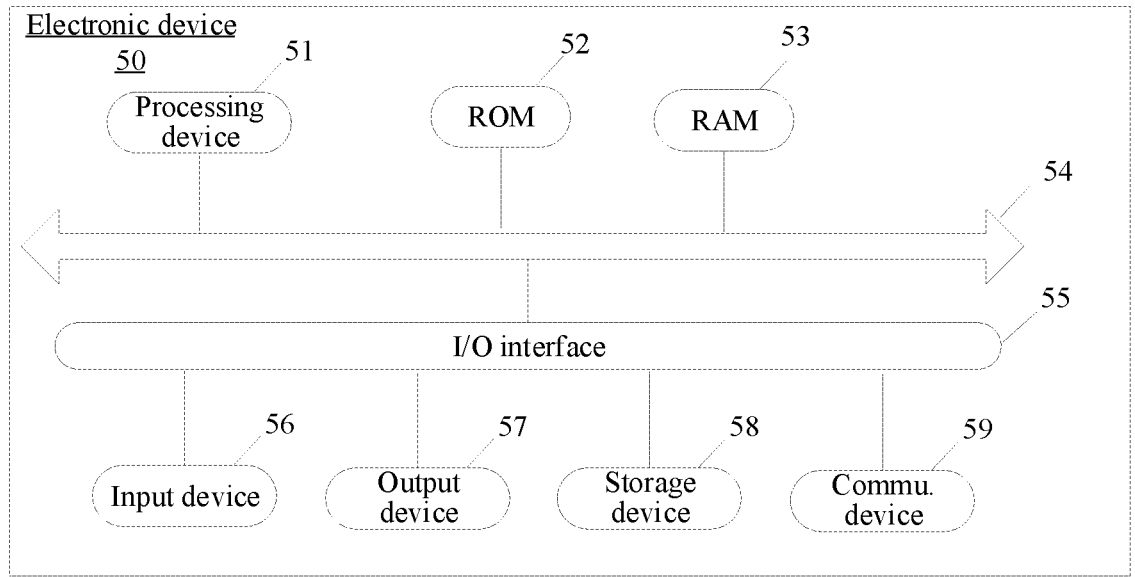
FIG. 5 is a schematic diagram of a hardware structure of an electronic device provided by an embodiment of the present disclosure.

Referring to FIG. 5, a schematic structural diagram of an electronic device 50 suitable for implementing the embodiment of the present disclosure is shown, wherein the electronic device 50 may be a terminal device or a server. Among them, the terminal device may include, but is not limited to, a mobile terminal such as a mobile phone, a notebook computer, a digital broadcast receiver, a PDA (personal digital assistant), a PAD (tablet computer), a PMP (portable multimedia player), a vehicle terminal (e.g., a car navigation terminal), and the like, and a fixed terminal such as a digital TV, a desktop computer, and the like. The electronic device shown in FIG. 5 is only an example, and should not bring any limitation to the functions and the scope of use of the embodiments of the present disclosure.

As shown in FIG. 5, the electronic device 50 can include a processing device (e.g., central processing unit, graphics processor and so on) 51 that can perform various appropriate actions and processes in accordance with a program stored in a read-only memory (ROM) 52 or a program loaded from a storage device 58 into a random access memory (RAM) 53. In the RAM 53, various programs and data necessary for the operation of the electronic device 50 are also stored. The processing device 51, the ROM 52, and the RAM 53 are connected to each other through a bus 54. An input/output (I/O) interface 55 is also connected to bus 54.

Generally, the following devices can be connected to the I/O interface 55: input device 56 including, for example, a touch screen, a touch pad, a keyboard, mouse, a camera, a microphone, accelerometer, gyroscope and the like; an output device 57 including, for example, a Liquid Crystal Display (LCD), a speaker, a vibrator, and the like; storage device 58 including, for example, magnetic tape, hard disk and the like; and a communication device (Commu. device) 59. The communication device 59 can allow the electronic device 50 to communicate with other devices, either wirelessly or by wire, to exchange data. While FIG. 5 illustrates an electronic device 50 having various means, it is to be understood that not all illustrated means are required to be implemented or provided. More or fewer devices can be alternatively implemented or provided.

In particular, the processes described above with reference to the flow diagrams can be implemented as computer software programs, according to embodiments of the present disclosure. For example, embodiments of the present disclosure include a computer program product including a computer program carried on a computer readable medium, the computer program containing program code for performing the method illustrated by the flow chart. In such an embodiment, the computer program can be downloaded and installed from a network via the communication device 59, or installed from the storage device 58, or installed from the ROM 52. The computer program, when executed by the processing device 51, performs the above-described functions defined in the methods of the embodiments of the present disclosure.

It should be noted that the computer readable medium of the present disclosure can be a computer readable signal medium or a computer readable storage medium or any combination of the two. A computer readable storage medium can be, for example, but not limited to, an electronic, magnetic, optical, electromagnetic, infrared, or semiconductor system, device, or device, or any combination of the foregoing. More specific examples of the computer readable storage medium can include, but are not limited to: an electrical connection having one or more wires, a portable computer diskette, a hard disk, a random access memory (RAM), a read-only memory (ROM), an erasable programmable read-only memory (EPROM or flash memory), an optical fiber, a portable compact disc read-only memory (CD-ROM), an optical storage device, a magnetic storage device, or any suitable combination of the foregoing. In the present disclosure, a computer readable storage medium can be any tangible medium that can contain, or store a program for use by or in connection with an instruction execution system, device, or device. In contrast, in the present disclosure, a computer readable signal medium can include a propagated data signal with computer readable program code embodied therein, for example, in baseband or as part of a carrier wave. Such a propagated data signal can take any of a variety of forms, including, but not limited to, electromagnetic, optical, or any suitable combination thereof. A computer readable signal medium can be any computer readable medium that is not a computer readable storage medium and that can communicate, propagate, or transport a program for use by or in connection with an instruction execution system, device, or device. Program code embodied on a computer readable medium can be transmitted using any appropriate medium, including but not limited to: electrical wires, optical cables, radio frequency (RF) and so forth, or any suitable combination of the foregoing.

The computer readable medium can be embodied in the electronic device or can be separate and not incorporated into the electronic device.

The computer readable medium carries one or more programs which, when executed by the electronic device, cause the electronic device to perform the method shown in the above embodiment.

Computer program code for carrying out operations for aspects of the present disclosure can be written in any combination of one or more programming languages, including but not limited to an object oriented programming language such as Java, Smalltalk, C++, including conventional procedural programming languages, such as the "C" programming language or similar programming languages. The program code can execute entirely on the user's computer, partly on the user's computer, as a stand-alone software package, partly on the user's computer and partly on a remote computer or entirely on the remote computer or server. In the scenario relating to remote computer, the remote computer can be connected to the user's computer through any type of network, including a Local Area Network (LAN) or a Wide Area Network (WAN), or the connection can be made to an external computer (for example, through the Internet using an Internet service provider).

The flowchart and block diagrams in the figures illustrate the architecture, functionality, and operation of possible implementations of systems, methods and computer program products according to various embodiments of the present disclosure. In this regard, each block in the flowchart or block diagrams can represent a module, a segment of program, or a portion of code, which includes one or more executable instructions for implementing the specified logical function. It should also be noted that, in some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The units described in the embodiments of the present disclosure can be implemented by software or hardware. The name of a unit does not in some cases constitute a limitation of the unit itself.

The functions described herein above can be performed, at least in part, by one or more hardware logic components. For example, without limitation, exemplary types of hardware logic components that can be used include: field Programmable Gate Arrays (FPGA), Application Specific Integrated Circuits (ASIC), Application Specific Standard Products (ASSP), system on a chip (SOC), Complex Programmable Logic Devices (CPLD), and the like.

In the context of this disclosure, a machine-readable medium can be a tangible medium that can contain, or store a program for use by or in connection with an instruction execution system, device, or device. The machine-readable medium can be a machine-readable signal medium or a machine-readable storage medium. A machine-readable medium can include, but is not limited to, an electronic, magnetic, optical, electromagnetic, infrared, or semiconductor system, device, or device, or any suitable combination of the foregoing. More specific examples of a machine-readable storage medium would include an electrical connection based on one or more wires, a portable computer diskette, a hard disk, a random access memory (RAM), a read-only memory (ROM), an erasable programmable read-only memory (EPROM or flash memory), an optical fiber, a portable compact disc read-only memory (CD-ROM), an optical storage device, a magnetic storage device, or any suitable combination of the foregoing.

In a first aspect, according to one or more embodiments of the present disclosure, a data processing method applied to a wearable device is provided, wherein the data processing method includes: acquiring exercise data of a user in a preset time period and a physical parameter preset by the user, wherein the exercise data includes exercise data of a head, a hand and a leg of the user; and inputting the exercise data and the physical parameter into a pre-trained energy determination model for processing to obtain energy consumed by the user in the preset time period.

According to one or more embodiments of the present disclosure, the inputting the exercise data and the physical parameter into a pre-trained energy determination model for processing to obtain energy consumed by the user in the preset time period includes: in the energy determination model, adopting a pre-trained multivariate linear regression submodel to determine an exercise coefficient based on the exercise data; determining a basal metabolic rate of the user based on the physical parameter; and determining the energy consumed by the user in the preset time period based on the exercise coefficient and the basal metabolic rate.

According to one or more embodiments of the present disclosure, the data processing method further includes training a multivariate linear regression submodel to obtain the pre-trained multivariate linear regression submodel by: acquiring a training sample and label data corresponding to the training sample, wherein the training sample is used as the exercise data of a sample, and the label data is the exercise coefficient corresponding to the training sample; inputting the training sample into a multiple linear regression submodel for processing to obtain a predicted exercise coefficient; and adjusting a model parameter of the multivariate linear regression submodel based on the predicted exercise coefficient and a loss value of the label data to obtain a trained multivariate linear regression submodel.

According to one or more embodiments of the present disclosure, the model parameter of multiple linear regression submodel is greater than 0.

According to one or more embodiments of the present disclosure, the acquiring exercise data of a user in a preset time period includes: acquiring inertial measurement data, the inertial measurement data being acquired by the wearable device of the user; and determining the exercise data based on the inertia measurement data.

According to one or more embodiments of the present disclosure, the inertial measurement data includes the inertial measurement data of the head-mounted display, the inertia measurement data of the handle and the inertial measurement data of the leg tracking device.

According to one or more embodiments of the present disclosure, the determining the exercise data based on the inertial measurement data including at least one of:
    determining a moving distance, a square of an average linear velocity and a square of an average angular velocity of the head-mounted display in the preset time period based on the inertial measurement data of the head-mounted display;
    determining a total moving distance, an average linear speed and an average angular speed of the handle based on the inertia measurement data of the handle; and
    determining a square of an average angular velocity and a square of an average acceleration of the leg tracking device from the inertial measurement data of the leg tracking device.

In a second aspect, according to one or more embodiments of the present disclosure, a data processing device applied to a wearable device is provided, wherein the data processing device includes:
    an acquisition unit configured to acquire exercise data of a user in a preset time period and a physical parameter preset by the user, wherein the exercise data includes exercise data of a head, a hand and a leg of the user; and
    a processing unit configured to input the exercise data and the physical parameter into a pre-trained energy determination model for processing to obtain energy consumed by the user in the preset time period.

In a third aspect, according to one or more embodiments of the present disclosure, an electronic device is provided, including at least one processor and a memory;
    the memory stores computer-executable instructions;
    the at least one processor execute the computer-executable instructions stored by the memory to cause the at least one processor to perform the data processing method provided by the above first aspect.

In a fourth aspect, according to one or more embodiments of the present disclosure, a non-transitory computer readable storage medium is provided, the computer readable storage medium has stored thereon computer executable instructions which, when executed by a processor, implement the data processing method provided by the above first aspect.

In a fifth aspect, according to one or more embodiments of the present disclosure, a computer program product is provided, the computer program product includes computer executable instructions which, when executed by a processor, implement the data processing method provided by the above first aspect.

The foregoing description is only exemplary of the preferred embodiments of the disclosure and is illustrative of the principles of the technology employed. It will be understood by those skilled in the art that the scope of the disclosure herein is not limited to the particular combination of features described above, but also encompasses other combinations of features described equivalents thereof without departing from the spirit of the disclosure. For example, the above features and the technical features disclosed in the present disclosure (but not limited to) having similar functions are replaced with each other to form the technical solution.

Further, while operations are depicted in a particular order, this should not be understood as requiring that such operations be performed in the particular order shown or in sequential order. Under certain circumstances, multitasking and parallel processing may be advantageous. Likewise, while several specific implementation details e included in the above discussion, these should not be construed as limitations on the scope of the disclosure. Certain features that are described in the context of separate embodiments can also be implemented in combination in a single embodiment. Conversely, various features that are described in the context of a single embodiment can also be implemented in multiple embodiments separately or in any suitable subcombination.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A data processing method applied to a wearable device, wherein the data processing method comprises:

acquiring exercise data of a user in a preset time period and a physical parameter preset by the user, wherein the exercise data comprises exercise data of a head, a hand and a leg of the user; and inputting the exercise data and the physical parameter into a pre-trained energy determination model for processing to obtain energy consumed by the user in the preset time period, wherein the pre-trained energy determination model comprises a pre-trained multivariate linear regression submodel, and the method further comprises training a multivariate linear regression submodel to obtain the pre-trained multivariate linear regression submodel by:

acquiring a training sample and label data corresponding to the training sample, wherein the training sample is used as the exercise data of a sample, and the label data is the exercise coefficient corresponding to the training sample;

inputting the training sample into a multiple linear regression submodel for processing to obtain a predicted exercise coefficient; and adjusting a model parameter of the multivariate linear regression submodel based on the predicted exercise coefficient and a loss value of the label data to obtain the pre-trained multivariate linear regression submodel.

2. The data processing method of claim 1, wherein the inputting the exercise data and the physical parameter into a pre-trained energy determination model for processing to obtain energy consumed by the user in the preset time period comprises:

in the energy determination model, adopting the pre-trained multivariate linear regression submodel to determine an exercise coefficient based on the exercise data;

determining a basal metabolic rate of the user based on the physical parameter; and determining the energy consumed by the user in the preset time period based on the exercise coefficient and the basal metabolic rate.

3. The data processing method of claim 1, wherein the model parameter of the multiple linear regression submodel is greater than 0.

4. The data processing method of claim 1, wherein the acquiring exercise data of a user in a preset time period comprises:

acquiring inertial measurement data, the inertial measurement data being acquired by the wearable device of the user; and determining the exercise data based on the inertia measurement data.

5. The data processing method of claim 4, wherein the wearable device comprising: a head-mounted display, a handle, a leg tracking device attached to the leg of the user, the handle and the leg tracking device are in communication connection with the head-mounted display, and the head-mounted display, the handle, and the leg tracking device comprise an inertial measurement sensor, respectively.

6. The data processing method of claim 5, wherein the determining the exercise data based on the inertial measurement data comprising at least one of:

determining a moving distance, a square of an average linear velocity and a square of an average angular velocity of the head-mounted display in the preset time period based on the inertial measurement data of the head-mounted display;

determining a total moving distance, an average linear speed and an average angular speed of the handle based on the inertia measurement data of the handle; or determining a square of an average angular velocity and a square of an average acceleration of the leg tracking device from the inertial measurement data of the leg tracking device.

7. An electronic device, comprising at least one processor and a memory;

the memory stores computer-executable instructions;

the at least one processor execute the computer-executable instructions stored by the memory to cause the at least one processor to:

acquire exercise data of a user in a preset time period and a physical parameter preset by the user, wherein the exercise data comprises exercise data of a head, a hand and a leg of the user; and input the exercise data and the physical parameter into a pre-trained energy determination model for processing to obtain energy consumed by the user in the preset time period, wherein the pre-trained energy determination model comprises a pre-trained multivariate linear regression submodel, and the computer-executable instructions, when executed by a computer processor, further cause the computer processor to: train a multivariate linear regression submodel to obtain the pre-trained multivariate linear regression submodel by:

acquiring a training sample and label data corresponding to the training sample, wherein the training sample is used as the exercise data of a sample, and the label data is the exercise coefficient corresponding to the training sample;

inputting the training sample into a multiple linear regression submodel for processing to obtain a predicted exercise coefficient; and adjusting a model parameter of the multivariate linear regression submodel based on the predicted exercise coefficient and a loss value of the label data to obtain the pre-trained multivariate linear regression submodel.

8. The electronic device of claim 7, wherein the computer-executable instructions, when executed by a computer processor, further cause the computer processor to:

in the energy determination model, adopt the pre-trained multivariate linear regression submodel to determine an exercise coefficient based on the exercise data;

determine a basal metabolic rate of the user based on the physical parameter; and determine the energy consumed by the user in the preset time period based on the exercise coefficient and the basal metabolic rate.

9. The electronic device of claim 7, wherein the model parameter of the multiple linear regression submodel is greater than 0.

10. The electronic device of claim 7, wherein the computer-executable instructions, when executed by a computer processor, further cause the computer processor to:

acquire inertial measurement data, the inertial measurement data being acquired by the wearable device of the user; and determine the exercise data based on the inertia measurement data.

11. The electronic device of claim 10, wherein the wearable device comprising: a head-mounted display, a handle, a leg tracking device attached to the leg of the user, the handle and the leg tracking device are in communication connection with the head-mounted display, and the head-mounted display, the handle, and the leg tracking device comprise an inertial measurement sensor, respectively.

12. The electronic device of claim 11, wherein the computer-executable instructions, when executed by a computer processor, further cause the computer processor to perform at least one of:

determining a moving distance, a square of an average linear velocity and a square of an average angular velocity of the head-mounted display in the preset time period based on the inertial measurement data of the head-mounted display;

determining a total moving distance, an average linear speed and an average angular speed of the handle based on the inertia measurement data of the handle; or determining a square of an average angular velocity and a square of an average acceleration of the leg tracking device from the inertial measurement data of the leg tracking device.

13. A non-transitory computer readable storage medium having stored thereon computer executable instructions which, when executed by a processor, cause the computer processor to:

acquire exercise data of a user in a preset time period and a physical parameter preset by the user, wherein the exercise data comprises exercise data of a head, a hand and a leg of the user; and input the exercise data and the physical parameter into a pre-trained energy determination model for processing to obtain energy consumed by the user in the preset time period, wherein the pre-trained energy determination model comprises a pre-trained multivariate linear regression submodel, and the computer-executable instructions, when executed by a computer processor, further cause the computer processor to train a multivariate linear regression submodel to obtain the pre-trained multivariate linear regression submodel by:

acquiring a training sample and label data corresponding to the training sample, wherein the training sample is used as the exercise data of a sample, and the label data is the exercise coefficient corresponding to the training sample;

inputting the training sample into a multiple linear regression submodel for processing to obtain a predicted exercise coefficient; and adjusting a model parameter of the multivariate linear regression submodel based on the predicted exercise coefficient and a loss value of the label data to obtain the pre-trained multivariate linear regression submodel.

14. The storage medium of claim 13, wherein the computer-executable instructions, when executed by a computer processor, further cause the computer processor to: the computer-executable instructions, when executed by a computer processor, further cause the computer processor to:

in the energy determination model, adopting the pre-trained multivariate linear regression submodel to determine an exercise coefficient based on the exercise data;

determining a basal metabolic rate of the user based on the physical parameter; and determining the energy consumed by the user in the preset time period based on the exercise coefficient and the basal metabolic rate.

15. The storage medium of claim 13, wherein the computer-executable instructions, when executed by a computer processor, further cause the computer processor to:

acquire inertial measurement data, the inertial measurement data being acquired by the wearable device of the user; and determine the exercise data based on the inertia measurement data.

16. The storage medium of claim 15, wherein the wearable device comprising: a head-mounted display, a handle, a leg tracking device attached to the leg of the user, the handle and the leg tracking device are in communication connection with the head-mounted display, and the head-mounted display, the handle, and the leg tracking device comprise an inertial measurement sensor, respectively.

17. The storage medium of claim 16, wherein the computer-executable instructions, when executed by a computer processor, further cause the computer processor to perform at least one of:

determining a moving distance, a square of an average linear velocity and a square of an average angular velocity of the head-mounted display in the preset time period based on the inertial measurement data of the head-mounted display;

determining a total moving distance, an average linear speed and an average angular speed of the handle based on the inertia measurement data of the handle; or determining a square of an average angular velocity and a square of an average acceleration of the leg tracking device from the inertial measurement data of the leg tracking device.

* * * * *